Feb. 11, 1975 F. E. TRIPLETT Plant Pat. 3,686
GRAPEVINE
Filed Jan. 2, 1974
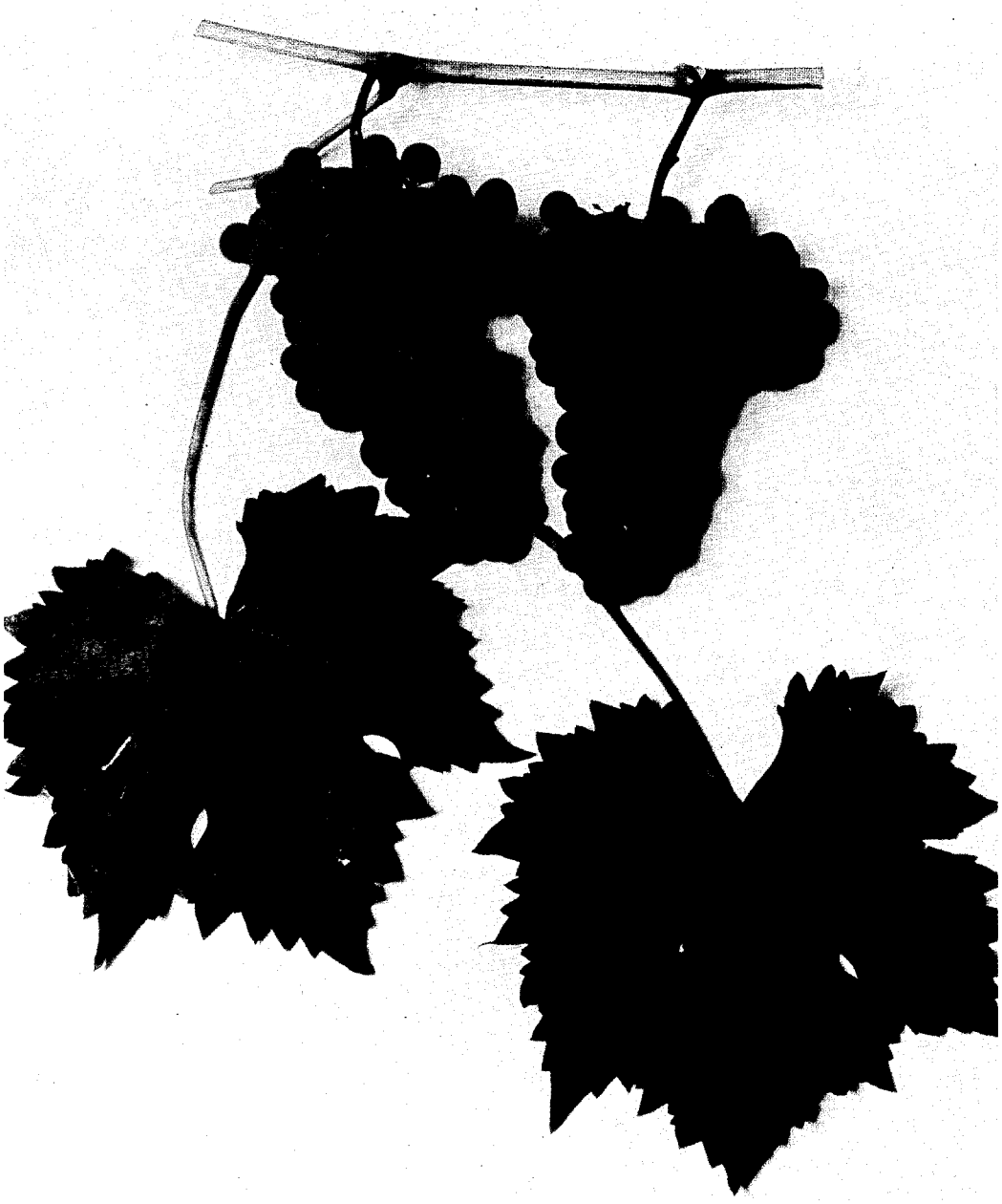

United States Patent

Plant Pat. 3,686

Patented Feb. 11, 1975

3,686

GRAPEVINE

Fay E. Triplett, 749 E. Keyes Road
Ceres, Calif. 95307

Filed Jan. 2, 1974, Ser. No. 430,033
Int. Cl. A01h *5/03*
U.S. Cl. Plt.—47 1 Claim

ABSTRACT OF THE DISCLOSURE

A table-wine variety of grapevine—adaptable to relatively warm growing regions—which is of medium vigor, upright, medium dense, hardy, foliated with medium size, thick, cordate leaves, and productive of medium size, long conical clusters of medium size, black, uniform, spherical berries having a bluish bloom; the berries surgaring early and high while retaining high acid and low pH, ripening early to mid-season, and being easy to harvest, readily and cleanly dropping free under the impact of a mechanical harvester.

BACKGROUND OF THE VARIETY

In contemplation of the need for improved table-wine varieties of grapevines, and particularly those adaptable to mechanical harvesting, I have—in my vineyard located near Ceres, Stanislaus County, Calif.—undertaken experimental breeding of grapevines for such purpose. The present variety resulted from my endeavors in conducting such experimental breeding program.

ORIGIN OF THE VARIETY

The present variety of grapevine was originated by me, in my aforesaid vineyard, as a first generation cross between Ruby Cabernet as the seed parent, and Joannes Seyve 26205 as the pollen parent. Neither the Ruby Cabernet nor the Joanes Seyve 26205 is patented.

ASEXUAL REPRODUCTION OF THE VARIETY

Subsequent to its origination by me, I asexually reproduced the present variety of grapevine in my vineyard, located as aforesaid, by cuttings as well as top-working, and—in maturity—such reproductions ran true to the original grapevine in all respects.

SUMMARY OF THE VARIETY

The present table-wine variety of grapevine is of medium vigor, upright, medium dense, hardy, foliated with medium size, thick, cordate leaves, and productive of medium size, long conical clusters of medium size, black, uniform, spherical berries having a bluish bloom; the berries sugaring early and high while retaining high acid and low pH, ripening early to mid-season, and being easy to harvest, readily and cleanly dropping free under the impact of a mechanical harvester. Further, the variety evidences more than ordinary resistance to mildew, and no tendency to rot even though the clusters remain on the vine somewhat beyond the normal harvest period.

The present variety of grapevine is distinctively characterized, in comparison to the Ruby Cabernet, essentially as follows:

BRIEF DESCRIPTION OF THE DRAWING

The drawing is an illustration, by photographic reproduction in color, of grape clusters, together with leaves.

DESCRIPTION OF THE VARIETY

The botanical details of this new and distinct variety of grapevine—with color definitions (except those in common color terms) referenced to Maerz and Paul Dictionary Of Color—are as follows:

Vine:
- *Size.*—Medium.
- *Growth.*—Upright.
- *Density.*—Medium.
- *Hardiness.*—Hardy.
- *Productivity.*—Productive.

Trunk: Medium size; medium caliper
- *Bark.*—Adherent; shreddy.

Canes: Medium length; medium number; medium thicknesses; light brown (13–J–8); straight.
- *Nodes.*—Angular.
- *Internodes.*—Medium length.
- *Tendrils.*—Intermittent; medium thickness; medium length; bifurcated; smooth.

Flowers: Fertile.
- *Blooming period.*—Medium—May 10th–May 25th depending on seasonal conditions.
- *Stamens.*—Upright.

Leaves: Medium size: W x L=198 sq. cm.; W/L ratio, 1.44; cordate; thick.
- *Color.*—Upper surface—Glossy dark green (24–L–6). Lower surface—Pale green (23–J–5).
- *Texture.*—Medium.
- *Pubescence.*—Abundant; short; upright. Hairs along all veins—very few in interveinal areas.
- *Lobes.*—Number—5, with very shallow inferior sinus. Terminal lobe—acuminate.
- *Petiolar sinus.*—Shallow; narrow; U–V shape.
- *Inferior sinus.*—Very shallow or nearly absent; narrow.
- *Superior sinus.*—Shallow; narrow.
- *Margin.*—Dentate.
- *Teeth.*—Medium depth; medium width.

Fruit:
- *Date of ripening.*—September 3rd–21st depending on seasonal conditions. Will hold on vine until early October.
- *Season.*—Early.
- *Keeping quality.*—Very good.
- *Shipping quality.*—Good.
- *Cluster.*—Medium size; weight per cluster—300–500 grams; medium length—average 6"; medium breadth—average 4¼"; tapering; regular; single shouldered; medium compact.
- *Peduncle.*—Long—1¾"–3¼"; medium thick; green; rarely any lignification.
- *Pedicel.*—Medium length; slender; warts.
- *Brush.*—Short; wine color.

Berries: Medium adherent. Medium size—1.8 grams per berry. Uniform. Round.

| | Present variety | Ruby Cabernet |
|---|---|---|
| Clusters | Long conical, single shouldered | Long conical, frequently winged. |
| Peduncle | Long, medium soft, easy to pick | Predominantly lignified, very hard, difficult to pick. |
| Brush | Short, with red veins | Medium length, with purplish veins. |
| Berries | Spherical, ripens early to mid-season in Central Valley of California—September 3rd to 21st. Distinct flavor, with high sugar and high acid. Medium adherence to pedicel, easy dislodgment of berries under impact from mechanical harvesters. | Spherical to elipsoidal, ripens mid-season to late in Central Valley of California September 21st to October 10th. Distinct flavor, but acrid. Firm adherence to pedicel, difficult dislodgment of berries under impact from mechanical harvesters. |
| Skin | Thin and moderately tender | Medium thick and tough. |
| Seeds | Rounded and dark brown | Oblong and light brown, with greenish tinge. |
| Leaves | Upper surface—dark green and glossy. Inferior lobes, indistinct. | Upper surface—green, slate-like. Lobes all distinct. |
| Bark | Short and shreddy | Long and fissured to stringy. |

*Color.*—Black to deep bluish purple (48–A–12), with medium thick, bluish bloom.

*Skin.*—Thin; medium texture; adheres to pulp.

*Flesh.*—Green (21–J–8); semi-translucent; soft; tender; juice—medium, clear, sprightly, distinct; quality—best.

*Test averages.*—Sugar content (Balling)—24.0. Total acid (grams per 100 cc.)—1.04. pH—3.46. The berries of the present variety develop a high sugar content at an early date without either lowering the acid or raising the pH excessively; these factors being most favorable in a table-wine variety of grapevine.

*Seeds.*—Separate from pulp easily. Average number per berry—2.88. Small; short; broad; slightly notched; short beaked; brown (8–H–6).

*Raphe.*—Cord-like; raised.

*Chalaza.*—Usually positioned above center; circular; distinct; well-formed, but small; raised, with pit in center.

*Use.*—Table wine.

The grapevine and its fruit herein described may vary in slight detail due to climatic and soil conditions under which the variety may be grown; the present description being of the variety as grown in the Central Valley of California.

I claim:

1. A new and distinct table-wine variety of grapevine, substantially as illustrated and described, which is of medium vigor, upright, medium dense, hardy, foliated with medium size, thick, cordate leaves, and productive of medium size, long conical clusters of medium size, black, uniform, spherical, easy to harvest berries having a bluish bloom; the berries sugaring early and high while retaining high acid and low pH, and ripening early to mid-season in comparison to mid-season to late ripening of the Ruby Cabernet.

No references cited.

ROBERT E. BAGWILL, Primary Examiner